US008975386B2

(12) United States Patent
Pereira

(10) Patent No.: US 8,975,386 B2
(45) Date of Patent: Mar. 10, 2015

(54) CRYSTALLINE FORMS OF A MACROLIDE, AND USES THEREFOR

(75) Inventor: David E. Pereira, Apex, NC (US)

(73) Assignee: Cempra Pharmaceuticals, Inc., Chapel Hill, NC (US)

( * ) Notice: Subject to any disclaimer, the term of this patent is extended or adjusted under 35 U.S.C. 154(b) by 364 days.

(21) Appl. No.: 13/636,510

(22) PCT Filed: Mar. 22, 2011

(86) PCT No.: PCT/US2011/029424
§ 371 (c)(1),
(2), (4) Date: Sep. 21, 2012

(87) PCT Pub. No.: WO2011/119604
PCT Pub. Date: Sep. 29, 2011

(65) Prior Publication Data
US 2013/0018008 A1 Jan. 17, 2013

Related U.S. Application Data

(60) Provisional application No. 61/316,063, filed on Mar. 22, 2010.

(51) Int. Cl.
*C07H 17/08* (2006.01)
*C07D 498/04* (2006.01)
*A61K 31/7048* (2006.01)

(52) U.S. Cl.
CPC .............. *C07H 17/08* (2013.01); *C07D 498/04* (2013.01); *A61K 31/7048* (2013.01)
USPC ....................................................... 536/17.4

(58) Field of Classification Search
None
See application file for complete search history.

(56) References Cited

U.S. PATENT DOCUMENTS

| | | | |
|---|---|---|---|
| 4,331,803 A | 5/1982 | Watanabe | |
| 4,474,768 A | 10/1984 | Bright | |
| 4,742,049 A | 5/1988 | Baker | |
| 5,444,051 A | 8/1995 | Agouridas | |
| 5,527,780 A | 6/1996 | Agouridas | |
| 5,543,400 A | 8/1996 | Agouridas | |
| 5,635,485 A | 6/1997 | Agouridas | |
| 5,656,607 A | 8/1997 | Agouridas | |
| 5,747,467 A | 5/1998 | Agouridas | |
| 5,760,233 A | 6/1998 | Agouridas | |
| 5,770,579 A | 6/1998 | Agouridas | |
| 5,834,428 A | 11/1998 | Drucker | |
| 5,985,844 A | 11/1999 | Heck | |
| 6,011,142 A | 1/2000 | Bonnet | |
| 6,020,521 A | 2/2000 | Randolph | |
| 6,028,181 A | 2/2000 | Or | |
| 6,096,714 A | 8/2000 | Agouridas | |
| 6,121,432 A | 9/2000 | Bonnet | |
| 6,395,710 B1 | 5/2002 | Chu | |
| 6,407,074 B1 | 6/2002 | Bronk | |
| 6,420,535 B1 | 7/2002 | Phan | |
| 6,437,106 B1 | 8/2002 | Stoner | |
| 6,440,941 B1 | 8/2002 | Denis | |
| 6,455,505 B2 | 9/2002 | Agouridas | |
| 6,515,116 B2 | 2/2003 | Suh | |
| 6,555,524 B2 | 4/2003 | Kaneko | |
| 6,664,238 B1 | 12/2003 | Su | |
| 6,777,393 B2 | 8/2004 | Bronk | |
| 6,809,188 B1 | 10/2004 | Suh | |
| 6,849,608 B2 | 2/2005 | Su | |
| 6,890,907 B2 | 5/2005 | Speirs | |
| 7,419,961 B2 | 9/2008 | Napoletano | |
| 7,601,695 B2 * | 10/2009 | Liang et al. | 514/29 |
| 8,791,080 B2 * | 7/2014 | Fernandes | 514/29 |
| 2002/0028781 A1 | 3/2002 | Agouridas | |
| 2003/0176327 A1 | 9/2003 | Cassell | |
| 2004/0009930 A1 | 1/2004 | Su | |
| 2005/0022242 A1 | 1/2005 | Rosetti | |
| 2005/0153905 A1 | 7/2005 | Burger | |
| 2005/0222427 A1 | 10/2005 | Sharpless | |
| 2006/0100164 A1 | 5/2006 | Liang et al. | |
| 2006/0264385 A1 | 11/2006 | Wang | |
| 2007/0167382 A1 | 7/2007 | Finkelstein et al. | |
| 2007/0197518 A1 | 8/2007 | Johnson | |
| 2008/0221048 A1 | 9/2008 | Woo | |
| 2008/0287376 A1 | 11/2008 | Das | |
| 2009/0075916 A1 | 3/2009 | Upadhyay | |
| 2009/0156517 A1 | 6/2009 | Zhang | |
| 2010/0216731 A1 | 8/2010 | Pereira | |

FOREIGN PATENT DOCUMENTS

| | | | |
|---|---|---|---|
| EP | 0248279 A2 | 12/1987 |
| EP | 1024145 A2 | 8/2000 |
| WO | 9830574 A1 | 7/1998 |
| WO | 9921866 A1 | 5/1999 |
| WO | 9928311 A1 | 6/1999 |
| WO | 0012521 A1 | 3/2000 |

(Continued)

OTHER PUBLICATIONS

PCT International Search Report and Written Opinion for PCT/US2011/029424, mailed May 5, 2011.
Jones, Ronald N., et al., MIC Quality Control Guidelines and Disk Diffusion Test Optimization for CEM-101, a Novel Fluoroketolide, 2010, Journal of Clinical Microbiology, vol. 48, No. 4, pp. 1470-1473.
Caira MR, "Crystalline polymorphism of orgainic compounds," Design of Organic Solids, Topics in Current Chemistry, Springer Berlin Heidelberg, 1998, p. 163-208.
Holzer, G., et al., "K$\alpha$1,2 and K$\beta$1,3 X-Ray Emission Lines of the 3d Transition Metals", Dec. 1997, Physical Review, vol. 56, No. 6, pp. 4554-4568.
LeMahieu, R. A., Carson, M., and Kierstead, R. W., 'Glycoside Cleavage Reactions on erythromycin A. Preparation of Erythronolide A,' Journal of Medicinal Chemistry, vol. 17, No. 9, 1974, 953-956.
Romero et al., 'An efficient entry to new sugar modified ketolide antibiotics' Tetrahedron Letters, vol. 46, 2005, pp. 1483-1487.

(Continued)

*Primary Examiner* — Eric Olson
(74) *Attorney, Agent, or Firm* — Brannon Sowers & Cracraft PC

(57) ABSTRACT

New crystalline forms of macrolide compounds, and pharmaceutical compositions thereof, are described herein. In addition, processes for preparing the crystalline forms are described herein.

14 Claims, 2 Drawing Sheets

(56) References Cited

FOREIGN PATENT DOCUMENTS

| WO | 0044761 A2 | 8/2000 |
|---|---|---|
| WO | 0062783 A2 | 10/2000 |
| WO | 0250092 A1 | 6/2002 |
| WO | 03004509 | 1/2003 |
| WO | 03004509 A2 | 1/2003 |
| WO | 03072141 A1 | 9/2003 |
| WO | 2004080391 A2 | 9/2004 |
| WO | 2005105821 | 11/2005 |
| WO | WO2009/055557 | 4/2009 |

OTHER PUBLICATIONS

Birkenmeyer, R. D., Kroll, S. J., Lewis, C., Stern, K. F., and Zurenko, G. E., 'Synthesis and Antibacterial Activity of Clindamycin Analogues: Pirlimycin, a Potent Antibacterial Agent', Journal of Medicinal Chemistry, vol. 27, No. 2, 1984, 216-223.
Vince, R., Almquist, R. G., Ritter, C. L., and Deluge, S., Antimicrobial Agents and Chemotherapy, vol. 8, No. 4, 1975, 439-443.
Or et al., 'Design, Synthesis, and Antimicrobial Activity of 6-0-Substituted Ketolides Active Against Resistant Respiratory Tract Pathogens', J. Med. Chem., 43:1045-49 (2000).
Champney et al., 'Structure-Activity Relationships for Six Ketolide Antibiotics', Current Microbiology, 42:203-10 (2001).
Denis et al., beta-Keto-Ester Chemistry and Ketolides. Snythesis and antibacterial Activity of 2-Halogeno, 2-Methyl and 2,3 Enol-Ether Ketolides, Bioorganic & Medicinal Chemistry Letters, 10:2019-22 (2000).
Torne et al. 'Peptidotriazoles on Solid Phase: [1,2,3]-Triazoles by Regiospecific Copper(I)-Catalyzed 1,3-Dipolar Cycloadditions of Terminal Alkynes to Azides', J. Org. Chem., 67:3057-64 (2002).
Rostovtsev, V.V. et al., 'A Stepwise Huisgen Cycloaddition Process: Copper(I)=Catalyzed Regioselective 'Ligation' of Azides and Terminal Alkynes,' Angew. Chem. Int. Ed., 41: 2596-2599 (2002).
Baker, W.R. et al., 'Modification of macrolide antibiotics. Synthesis of 11-deoxy-11-(carboxyamino)-6-0-methylerythromycin A 11,12-(cyclic esters) via an intramolecular Michael reaction of O-carbamates with an alpha, beta -unsaturated ketone,' J. Org. Chem., 53:2340-2345, 1988.
Djokic, S. et al., 'Erythromycin Series. Part 11. Ring Expansion of Erythromycin A Oxime by the Beckmann Rearrangement.' J. Chem. Soc Perkin Trans 1., 1881-1890 (1986).
Phan, L.T. et al., 'Synthesis of 2-Fluoro-6-O-propargyl-11,12-carbamate Ketolides. A Novel Class of Antibiotics,' Org. Ltrs., 2:2951-2954 (2000).
Liang C. H. et al., 'Synthesis and biological activity of new 5-0-sugar modified ketolide and 2-fluoro-ketolide antibiotics,' Bioorganic & Medicinal Chemistry Letters, Pergamon, Elsevier Science, GB, vol. 15, No. 5, Mar. 1, 2005, pp. 1307-1310.
Plata et al., "The synthesis of ketolide antibiotic ABT-773 (cethromycin)," Tetrahedron, vol. 60, 2004, pp. 10171-10180.
Ma et al., Curr. Med. Chem., "Anti-Infective Agents," vol. 1, 2002, pp. 15-34.
Berge, Stephen M., et al., "Pharmaceutical Salts", 1977, Journal of Pharmaceutical Sciences, vol. 66, No. 1, pp. 1-19
Bermudez, Luiz E., et al., "Telithromycin is Active Against *Mycobacterium avium* in Mice Despite Lacking Significant Activity in Standard In Vitro and Macrophage Assays and Is Associated with Low Frequency of Resistance During Treatment", 2001, Antimicrobal Agents and Chemotherapy, vol. 45, No. 8, pp. 2210-2214.
Bermudez, Luiz E., et al., "EDP-420, a Bicyclolide (Bridged Bicyclic Macrolide), Is Active Against *Mcyobacterium avium*", 2007, Antimicrobal Agents and Chemotherapy, vol. 51, No. 5, pp. 1666-1670.
Cynamon, M. H., et al., "Activity of ABT-773 Against *Mycobacterium avium* Complex in the Beige Mouse Model", 2000, Antimicrobal Agents and Chemotherapy, vol. 44, No. 10, pp. 2895-2896.

Patel, Ramesh N., "Stereoselective Biocatalysis", 2000, Bristol-Myers Squibb Research Institute; pp. 775-797.
Vennerstrom, Jonathan L., et al., "Identification of an Antimalarial Synthetic Trioxolane Drug Development Candidate", 2004, Letters to Nature, vol. 430, pp. 900-904.
Barcia-MaCay, Maritza, et al., 'Pharmacodynamic Evaluation of the Intracellular Activities of Antibiotics Against *Staphylococcus aureus* in a Model of THP-1 Macrophages', 2006, Antimicrobial Agents and Chemotherapy. vol. 50, No. 3, pp. 841-851.
Bebear, C.M., et al., In vitro activity of trovafloxacin compared to those of five antimicrobials against mycoplasmas including *Mycoplasma hominis* and *Ureaplasma urealyticum* fluoroquinolone-resistant isolates that have been genetically characterized, Antimicrob Agents Chemother 44:2557-2560 (2000).
Duffy, L. et al., Fluoroquinolone resistance in *Ureaplasma parvum* in the United States, J Clin Microbiol 44:1590-1591 (2006).
Waites, K.B., et al., Mycoplasmas and ureaplasmas as neonatal pathogens, Clin Microbiol Rev 18:757-89 (2005).
Zuckerman, "Macrolides and ketolides: azithromycin, clarithromycin, telithromycin", Infectious Disease Clinics of North America, vol. 18, (2004), pp. 621-649.
Crone, Julia, et al., "Evaluation of a monoclonal antibody-based test for detection of *Helicobacter pylori*-Specific Antigen in stool samples from mice," Jul. 2004, Clinical and Diagnostic Laboratory Immunology, vol. 11, No. 4, pp. 799, 800.
Laine, Loren, et al., "Prospective comparison of H&E, Giemsa and Genta stains for the diagnosis of *Helicobacter pylori*," 1997, Gastrointestinal Endoscopy, vol. 45, No. 6, pp. 463-467.
Lee, Adrian, et al., "A standard mouse model of *Helicobacter pylori* infection: introducing the Sydney Strain," 1997, Gastroenterology, vol. 112, pp. 1386-1397.
Drusano, G. L., et al., "Is 60 Days of Ciprofloxacin Adminstration Necessary for Postexposure Prophylaxis for *Bacillus anthracis*?", 2008, Antimicrobial Agents and Chemotherapy. vol. 52, No. 11, pp. 3973-3979.
Eder, P. I., et al., 1991. Statistical Analysis of Dose-Response Experiments by Maximum Likelihood Analysis and Iteratively Reweighted Nonlinear Least Squares Regression Techniques, 1991, Drug Information Journal, vol. 28, pp. 323-334.
Inglesby, Thomas V., et al., "Anthrax as a Biological Weapon, 2002", 2002, Journal of the American Medical Association, vol. 287, No. 17, pp. 2236-2252.
Celebuski, J.E. et al., 'Chemical Modification of Erythromycin: Novel Reaction Observed by Treatment with Metalloporphyrins', vol. 35, No. 23, pp. 3837-3850, 1994, Elsevier Science Ltd.
Morimoto S. et al., 'Chemical Modification of Erythromycins VII. Molecular Rearrangement Observed During Chemical Modification Study of the Desosamine Unit of Erythromycins', Heterocycles, Elsevier Science Publishers, vol. 31, No. 2, Jan. 1, 1990, pp. 305-319.
Hill, D.R. et al., 'Novel Macrolides via meso-Tetraarylmetalloporphyrin Assisted Oxidation', Tetrahedron Letters, vol. 37, No. 6, pp. 787-790, 1996, Elsevier Science Ltd.
Physicians' Desk Reference, p. 2905, (2007).
Nilius et al.: 'Ketolides: the future of the macrolides?' Current Opinion in Pharmacology,[Online] vol. 2, Jan. 14, 2002, pp. 1-8 Retrieved from the Internet: <URL:http://www.sciencedirect.com/science/article/pii/S1471489202001984>.
Jensen, J. S., et al., Azithromycin Treatment Failure in *Mycoplasma genitalium* Positive Patients with Nongonococcal Urethritis Is Associated with Induced Macrolide Resistance, Clin Infect Dis 47:1546-53 (2008).
Li, X., et al., Emerging macrolide resistance in *Mycoplasma pneumoniae* in children: detection and characterization of resistant isolates, Pediatr Infect Dis J, 28 :693-696 (2009).
LeMaire, Sandrine, et al., "Cellular Accumulation and Pharmacodynamic Evaluation of the Intracellular Activity of CEM-101, a Novel Fluoroketolide, Against *Staphyllococcus aureus, Listeria Monocytogenes* and *Legionella pneumophila* in Human THP-1 Macrophages", 2009, Antimicrobial Agents and Chemotherapy. vol. 53, No. 9, pp. 3734-3743.

* cited by examiner

CRYSTALLINE FORMS OF A MACROLIDE, AND USES THEREFOR

CROSS-REFERENCE TO RELATED APPLICATIONS

This application is a U.S. national application under 37 C.F.R. §371(b) of International Application Serial No. PCT/US2011/029424 filed Mar. 22, 2011, which claims the benefit of U.S. provisional application 61/316,063, filed 22 Mar. 2010, the disclosures of which are incorporated by reference herein.

TECHNICAL FIELD

The invention described herein relates to a macrolide compound. More particularly, it relates to new crystalline forms of the macrolide compound, to processes for the preparation of the crystalline forms, and to pharmaceutical compositions containing the forms.

BACKGROUND AND SUMMARY OF THE INVENTION

It is appreciated that compounds considered as candidates for further development as pharmaceuticals advantageously possess desirable biological properties, but also physical properties that adapt them for use in the manufacture of pharmaceutical products. For example, compounds that form stable solids, including crystalline solids may be more readily manufactured and formulated. It is further appreciated that individual physical forms of the compound that are stable and additionally that may be prepared substantially free of other physical forms may also be more readily manufactured and formulated. It is to be understood herein that different physical forms may have markedly different physical properties, such as different solubility characteristics, different bioavailabilities and/or biological exposure, different stability, and the like.

In US patent application publication number US 2006/0100164, there are disclosed certain macrolide antibiotic compounds. The foregoing publication, and each additional publication cited herein is incorporated herein by reference. One of these macrolides is a fluoroketolide having Chemical Abstracts Registry Number 760981-83-7, which is also known as CEM-101 and solithromycin. The preparation of an amorphous form of CEM-101 is described therein. An alternative preparation of CEM-101 is described in WO 2009/055557. CEM-101 has the following chemical structure:

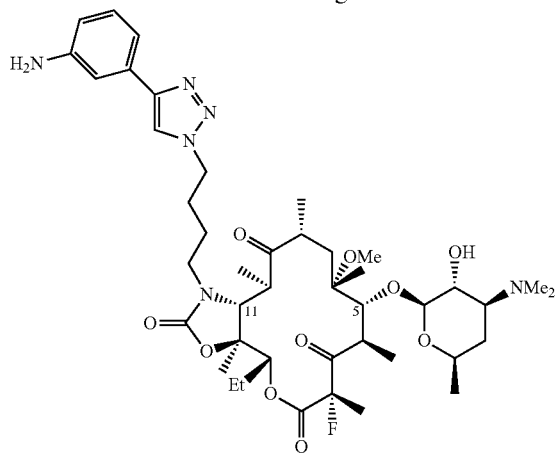

It has been discovered herein that CEM-101 can be isolated in a variety of crystalline forms which provide illustrative embodiments of the invention. CEM-101 can be isolated in crystalline form as a material having a range of different physical properties, depending upon the method of isolation. This is because CEM-101 can exist in more than one crystalline form, i.e., it exhibits polymorphism. CEM-101 can be isolated in at least two crystalline forms, denoted herein as Form I and Form II, each of which is pure or substantially pure and/or free of or substantially free of the other form. Various mixtures of Form I and Form II can also be isolated. In addition, solids which are mixtures of one ore more crystalline materials and also include amorphous solids can be obtained.

BRIEF DESCRIPTION OF THE DRAWINGS

Illustrative examples of X-ray powder diffraction (XRPD) spectra for each of Form I and Form II are given in FIG. 1 and FIG. 2, respectively, showing degrees 2θ on the X-axis and relative intensity on the Y-axis.

More detailed listings of the peaks for each of Form I and Form II are provided below in Tables 1-4 in the Examples, in which peaks are denoted as % relative intensity ($I/I_0 \times 100$). It is to be understood that in the X-ray powder diffraction spectra the exact values measured for °2θ (or the corresponding d-spacings) may vary depending upon the particular sample analyzed and the particular analysis procedure used. A range of values of at least ±0.1°2θ, and in some cases at least ±0.2°2θ, may be typical. Measurements on independently prepared samples on different instruments may lead to variability which is greater than ±0.1°2θ and/or ±0.2°θ.

DETAILED DESCRIPTION

Figure 1:
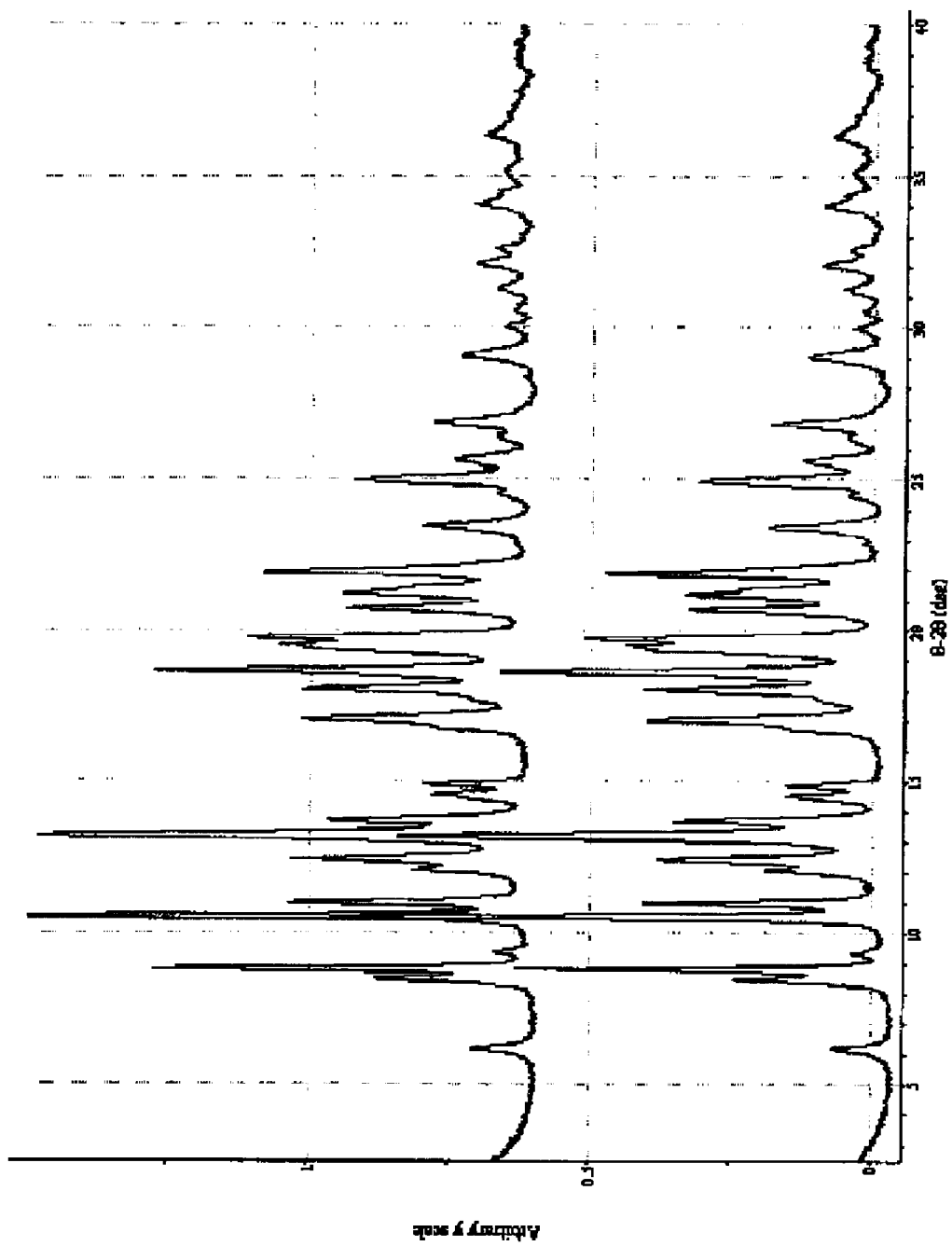

The new physical form, Form I of CEM-101 is a crystalline form which may be described by its X-ray powder diffraction pattern. Peaks at approximate positions of about °2θ=8.8, 10.5, 13.2 and 18.6 are representative of this crystalline form. An example of an X-ray powder diffraction spectrum for Form I is shown in FIG. 1. A more detailed analysis of the peaks is described in Tables 1-2 below. Form I of CEM-101 demonstrates minimal weight loss by thermogravimetric analysis (TGA). Water determination by Karl Fisher titration in typical lots is 0.6 to 1.1%. Dynamic vapor sorption indicates that the material is partially hygroscopic, but Form I solids are isolated upon desorption. Form I of CEM-101 melts at about 200° C. by DSC analysis.

As one embodiment there is described Form I of CEM-101 having an X-ray powder diffraction pattern with peaks at approximate positions of about °2θ=8.8, 10.5, 13.2 and 18.6. As another embodiment there is described a solid form of CEM-101 comprising Form I of CEM-101 having an X-ray powder diffraction pattern with peaks at approximate positions of about °2θ=8.8, 10.5, 13.2 and 18.6. As another embodiment there is described a composition comprising CEM-101, where the majority of CEM-101 is Form I of CEM-101 having an X-ray powder diffraction pattern with peaks at approximate positions of about °2θ=8.8, 10.5, 13.2 and 18.6. As another embodiment there is described CEM-101 in each of the foregoing embodiments having an X-ray powder diffraction pattern substantially the same as that of FIG. 1.

The new physical form, Form I, is physically stable and can be prepared substantially free of other physical forms, as described below. In one embodiment, there is described Form I of CEM-101 that is substantially free of Form II. The relative amounts of forms may be determined by a variety of analytical techniques, for example but not limited to, by the presence or absence of representative peaks, and/or by the relative peak heights and/or peak areas of appropriate discernable peaks in the XRPD spectrum. Form I of CEM-101, substantially free of other physical forms, may be characterized by an X-ray powder diffraction pattern with peaks at approximate positions of about °2θ=8.8, 10.5, 13.2 and 18.6. Peaks at about °2θ=6.2, 19.7 and/or 21.9 are also observed for this crystalline form. In another embodiment, there is described Form I of CEM-101 in each of the foregoing embodiments that is characterized by an X-ray powder diffraction pattern with peaks at approximate positions of about °2θ=8.8, 10.5, 13.2 and 18.6, and one or more additional peaks at about °2θ=6.2, 19.7 and/or 21.9. In another embodiment, there is described Form I of CEM-101 in each of the foregoing embodiments that is substantially free of Form II as determined by the X-ray powder diffraction pattern, wherein one or more peaks at °2θ=5.6, 9.8, and/or 11.7 are absent or nearly absent.

In another embodiment, pharmaceutical compositions that include CEM-101 are described, where the composition comprises or consists essentially of Form I of CEM-101, as described in each of the foregoing embodiments. In another embodiment, pharmaceutical compositions that include CEM-101 are described, where the composition comprises CEM-101, where the CEM-101 is at least about 60%, at least about 80%, at least about 90%, at least about 95%, at least about 98%, or at least about 99% Form I. In another embodiment, pharmaceutical compositions that include CEM-101 are described, where the composition comprises CEM-101, where the CEM-101 is substantially free of Form II. In another embodiment, pharmaceutical compositions that include Form I of CEM-101 are described, where the relative amount of Form II is less than about 40%, 20%, 10%, 5%, 2% or 1%. In another embodiment, pharmaceutical compositions that include CEM-101 are described, where the relative amount of Form I and Form II is determined by the relative peak heights of specific peaks. Illustrative relative peak height ratios for the peaks at °2θ=6.2 and °2θ=5.6 are a ratio of about 5:1 or more, about 10:1 or more, or about 20:1 or more. As another embodiment there is described Form I of CEM-101, substantially free of other physical forms. As another embodiment there is described a pharmaceutical composition comprising CEM-101 having an X-ray powder diffraction pattern substantially the same as that of FIG. 1.

Figure 2:
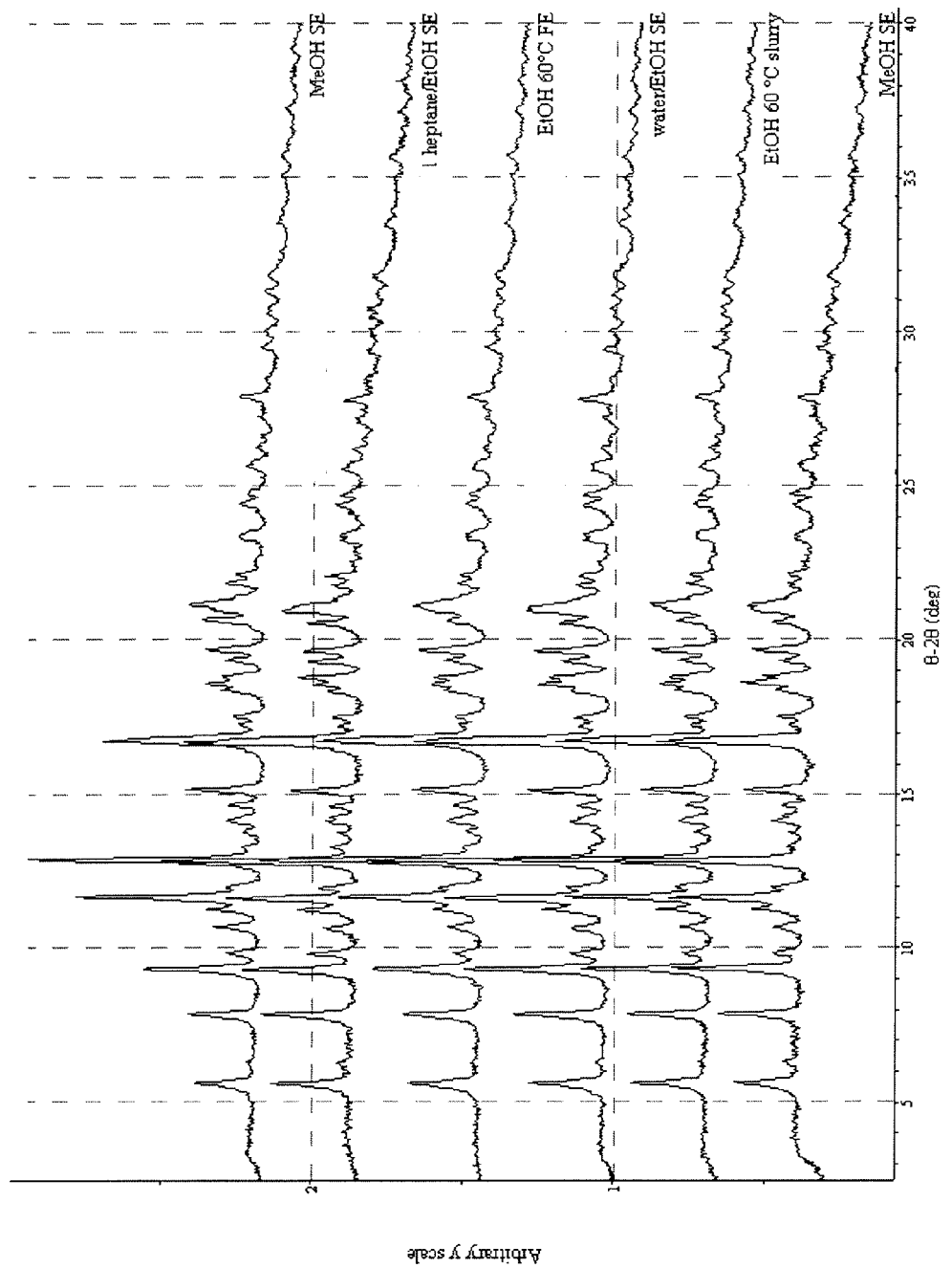

The new physical form, Form II of CEM-101 is a crystalline form which may be described by its X-ray powder diffraction pattern. Peaks at approximate positions of about °2θ=5.6, 7.9, 9.3, 11.7, 12.9 and 16.7 are representative of this crystalline form. An example of an X-ray powder diffraction spectrum for Form II is shown in FIG. 2. A more detailed analysis of the peaks is described in Tables 3-4 below. Based on a single crystal X-ray determination and dynamic vapor sorption analysis, Form II appears to be a non-hygroscopic anhydrous crystalline form that melts at about 225° C. as a single endothermic event by DSC analysis. It is appreciated herein that non-hygroscopic solids, such as Form II described herein, may be advantageous in the preparation of pharmaceutical compositions. Such advantages include improved handling and stability properties in manufacturing, improved lot to lot quality control.

As one embodiment there is described Form II of CEM-101 having an X-ray powder diffraction pattern with peaks at approximate positions of about °2θ=5.6, 7.9, 9.3, 11.7, 12.9 and 16.7. As another embodiment there is described a solid form of CEM-101, comprising Form II of CEM-101 having an X-ray powder diffraction pattern with peaks at approximate positions of about °2θ=5.6, 7.9, 9.3, 11.7, 12.9 and 16.7. As another embodiment there is described a composition comprising CEM-101, where the majority of CEM-101 is Form II of CEM-101 having an X-ray powder diffraction pattern with peaks at approximate positions of about °2θ=5.6, 7.9, 9.3, 11.7, 12.9 and 16.7. As another embodiment there is described CEM-101 in each of the foregoing embodiments having an X-ray powder diffraction pattern substantially the same as that of FIG. 2.

The new physical form, Form II, is physically stable and can be prepared substantially free of other physical forms, as described below. In one embodiment, there is described Form II of CEM-101 that is substantially free of Form I. The relative amounts of forms may be determined by a variety of analytical techniques, for example but not limited to, by the presence or absence of representative peaks, and/or by the relative peak heights and/or peak areas of appropriate discernable peaks in the XRPD spectrum. Form II of CEM-101, substantially free of other physical forms, may be characterized by an X-ray powder diffraction pattern with peaks at approximate positions of about °2θ=5.6, 7.9, 9.3, 11.7, 12.9 and 16.7. In another embodiment, there is described Form II of CEM-101 in each of the foregoing embodiments that is substantially free of Form I as determined by the X-ray powder diffraction pattern, wherein one or more peaks at °2θ=6.2 and/or 8.8 are absent or nearly absent.

In another embodiment, pharmaceutical compositions that include CEM-101 are described, where the composition comprises or consists essentially of Form II of CEM-101, as described in each of the foregoing embodiments. In another embodiment, pharmaceutical compositions that include CEM-101 are described, where the composition comprises CEM-101, where the CEM-101 is at least about 60%, at least about 80%, at least about 90%, at least about 95%, at least about 98%, or at least about 99% Form II. In another embodiment, pharmaceutical compositions that include Form II of CEM-101 are described, where the relative amount of Form I is less than about 40%, 20%, 10%, 5%, 2% or 1%. In another embodiment, pharmaceutical compositions that include CEM-101 are described, where the composition comprises CEM-101, where the CEM-101 is substantially free of Form I. In another embodiment, pharmaceutical compositions that include CEM-101 are described, where the relative amount of Form II and Form I is determined by the relative peak heights of specific peaks. Illustrative relative peak height ratios for the peaks at °2θ=5.6 and °2θ=6.2 are a ratio of about 5:1 or more, about 10:1 or more, or about 20:1 or more. As another embodiment there is described Form II of CEM-101, substantially free of other physical forms. Form II of CEM-101, substantially free of other physical forms, may be characterized by an X-ray powder diffraction pattern with peaks at approximate positions of about °2θ=5.6, 7.9, 9.3, 11.7, 12.9 and 16.7. As another embodiment there is described a pharmaceutical composition comprising CEM-101 having an X-ray powder diffraction pattern substantially the same as that of FIG. 2.

As a further embodiment there is described a pharmaceutical composition comprising CEM-101 in any ratio of Form I and Form II. As a further embodiment there is described a pharmaceutical composition comprising CEM-101 in any ratio of Form I and amorphous CEM-101. As a further embodiment there is described a pharmaceutical composition comprising CEM-101 in any ratio of Form II and amorphous CEM-101. As a further embodiment there is described a pharmaceutical composition comprising CEM-101 in any ratio of Form I and Form II and amorphous CEM-101.

Form I of CEM-101, including Form I substantially free of other physical forms, may be prepared by recrystallization as described below in the Examples, for example by a recrystallization procedure as described in Table A. Experiments 18, 21-23 and 26. In the table, the ratios of solvent to CEM-101 are given in a volume:weight ratio (mL/mg or L/g) where "T" indicates "times" of volume. In general, Form I may be obtained by adding a solution of CEM-101 in a water miscible, polar organic solvent, such as for example acetone, methanol or ethanol, to water to afford Form I of CEM-101.

According to one embodiment, described herein is a process for the preparation of Form I of CEM-101. The process includes the step of adding a solution of CEM-101 in a water miscible, polar organic solvent to water, such as at a temperature below 50° C. In addition, the process may include one or more of the following additional steps: heating the solution of CEM-101, filtering the solution of CEM-101, reducing the volume of the solution of CEM-101 by evaporation, stirring the water during the addition of the solution of CEM-101. In another embodiment, the prepared Form I of CEM-101 is substantially free of other physical forms. In another embodiment, the prepared Form I of CEM-101 is substantially free of Form II.

According to another embodiment, described herein is a process for the preparation of Form I of CEM-101, which comprises one or more of the steps of dissolving a source of CEM-101 in acetone, methanol or ethanol, or a combination thereof, optionally above ambient temperature, optionally filtering the solution, reducing the volume of the resultant solution by evaporation, adding the solution to water at a temperature below 50° C., optionally with stirring, and collecting the resulting crystalline solid. A further embodiment is one wherein the above solvent is acetone. A further embodiment is one wherein the above solvent is ethanol.

For any of the above processes a further embodiment is one wherein the solution is added to water at a temperature of about 10° C. to about 30° C. Another embodiment is one wherein the solution is added to water dropwise. In another embodiment the prepared Form I of CEM-101 is substantially free of other physical forms. In another embodiment the prepared Form I of CEM-101 is substantially free of Form II.

For any of the above processes for the preparation of Form I of CEM-101, any of the solvents acetone, methanol or ethanol, or a combination thereof may be used. In another embodiment, the organic solution is slowly added to water at about 20-30° C. In another embodiment, the volume:volume ratio of the organic solution to water is about 6 to about 15. In another embodiment, the volume:volume ratio of the organic solution to water is about 10 to about 13.

The above processes may be carried out with or without using seeds of Form I of CEM-101.

Form II of CEM-101, including Form II substantially free of other physical forms, may be prepared as described below in the Examples, for example by recrystallization as described in Table A. Experiments 1, 5, 6, 8, 9, 11, 12, 14, 16, 19 and 24, or by a slurry procedure as illustrated in Table B. In general, Form II may be obtained by adding water to a solution of CEM-101 in a water miscible, polar organic solvent. In addition, Form II of CEM-101 may be obtained by recrystallization from a number of organic solvents, with and without use of an antisolvent, and with or without use of seeding, as shown in Table A. Alternatively, a mixture of Form I and Form II may be converted into Form II of CEM-101 by slurrying the mixture in, for example, 2-propanol (isopropyl alcohol, IPA) at 60° C., or by slurrying the mixture in 2-butanone (methyl ethyl ketone, MEK) under a variety of conditions.

According to one embodiment, described herein is a process for the preparation of Form II of CEM-101. The process includes the step of adding water to a solution of CEM-101 in a water miscible, polar organic solvent. In addition, the process may include one or more of the following additional steps: filtering the solution of CEM-101, reducing the volume of the solution of CEM-101 by evaporation, stirring the solution of CEM-101 during addition of the water, and collecting the resulting crystalline solid. In another embodiment, the water miscible, polar organic solvent is protic. In another embodiment, the water miscible, polar organic solvent is aprotic. A further embodiment is one wherein the water miscible, polar organic solvent is acetone, acetonitrile, 1,4-dioxane, methanol or ethanol, or a combination thereof. A further embodiment is one wherein the solution of CEM-101 is above ambient temperature, for example about 65 to about 80° C. or about 65° C. A further embodiment is one wherein water at about ambient temperature is added to the solution. Another embodiment is one wherein water is added to the solution dropwise. In one embodiment of any of the above processes for the preparation of Form II of CEM-101 the volume:volume ratio of organic solvent to water is from about 1 to about 10. In another embodiment the prepared Form II of CEM-101 is substantially free of other physical forms.

The above processes may be carried out with or without using seeds of Form II of CEM-101.

For the above procedures, when a source of CEM-101 is a solid, it may be CEM-101 in amorphous form, as Form I or Form II, as a further crystalline form, as a glass, or as a mixture of any of those forms. It is to be understood that a solution of CEM-101 may also provide a source of CEM-101. As another embodiment, there is described a process of purifying CEM-101 comprising converting one or more forms or mixtures of forms of the CEM-101 into Form I or Form II substantially free of other physical forms. After such purification, it may be desired to convert CEM-101 into a different physical form for further use.

In another embodiment, described herein is a solid form of CEM-101 prepared by a process that includes the step of adding a solution of CEM-101 in a water miscible, polar organic solvent to water, such as at a temperature below 50° C. In addition, the process may include one or more of the following additional steps: optionally with heating, optionally filtering the solution, optionally reducing the volume of the resultant solution by evaporation, optionally with stirring, and collecting the resulting crystalline solid. In another embodiment, the water is at a temperature of about 10° C. to about 30° C. In another embodiment, the solvent is acetone, methanol or ethanol, or a combination thereof. In another embodiment, the organic solution is slowly added to water at about 20-30° C. In another embodiment, the volume:volume ratio of the organic solution to water is about 6 to about 15. In another embodiment, the volume:volume ratio of the organic solution to water is about 10 to about 13. In variations of the above, the process may include using seeds of Form I of CEM-101.

In another embodiment, described herein is a solid form of CEM-101 prepared by a process that includes the step of adding water to a solution of CEM-101 in a water miscible, polar organic solvent. In addition, the process may include one or more of the following additional steps: optionally filtering the solution, optionally reducing the volume of the resultant solution by evaporation, optionally with stirring, and collecting the resulting crystalline solid. In another embodiment, the water miscible, polar organic solvent is protic. In another embodiment, the water miscible, polar organic solvent is aprotic. A further embodiment is one wherein the water miscible, polar organic solvent is acetone, acetonitrile, 1,4-dioxane, methanol or ethanol, or a combination thereof. A further embodiment is one wherein the solution of the water miscible, polar organic solvent is above ambient temperature, for example about 65 to about 80° C. or about 65° C. A further embodiment is one wherein water at about ambient temperature is added to the solution. Another embodiment is one wherein water is added to the solution dropwise. In another embodiment, the volume:volume ratio of organic solvent to water is from about 1 to about 10. In variations of the above, the process may include using seeds of Form II of CEM-101.

As another embodiment, there is described a pharmaceutical composition comprising CEM-101 in crystalline form as described in any of the descriptions herein and further comprising at least one pharmaceutically acceptable carrier or excipient.

Illustratively, compositions may include one or more carriers, diluents, and/or excipients. The compounds described herein, or compositions containing them, may be formulated in a therapeutically effective amount in any conventional dosage forms appropriate for the methods described herein, and include one or more carriers, diluents, and/or excipients therefor. Such formulation compositions may be administered by a wide variety of conventional routes for the methods described herein, and in a wide variety of dosage formats, utilizing known procedures. Capsules and tablets are embodiments commonly used for oral administration of antibiotics. See generally, Remington: The Science and Practice of Pharmacy, ($21^{st}$ ed., 2005), as well as an illustrative formulation composition in the Examples.

As another embodiment, there is described a method of treatment of a bacterial infection, a protozoal infection, or a disorder related to a bacterial infection or protozoal infection comprising the step of administering to a subject in need thereof a therapeutically effective amount of CEM-101 in crystalline form as described herein, or a pharmaceutical composition thereof further comprising at least one pharmaceutically acceptable carrier or excipient. Illustrative dosing schedules include the daily administration of a composition, in a single or divided format, comprising about 1,200 mg, about 1,000 mg, about 800 mg, about 400 mg, about 200 mg, or about 100 mg.

As another embodiment, there is described a use of CEM-101 in crystalline form as described herein for the treatment of a bacterial infection, a protozoal infection, or a disorder related to a bacterial infection or protozoal infection.

As another embodiment, there is described a use of CEM-101 in crystalline form as described herein for the manufacture of a medicament for the treatment of a bacterial infection, a protozoal infection, or a disorder related to a bacterial infection or protozoal infection.

As a further embodiment, method or use described above is one wherein the subject is a mammal, a fish, a bird or a reptile. As another embodiment, there is described a method or use wherein the subject is a mammal. As another embodiment, there is described a method or use wherein the subject is a human.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

As shown in the interconversion of slurries experiment summarized below in the Examples in Table B, slurries of Forms I and II are prepared in 2-propanol (IPA) and 4-butanone (MEK) at ambient, sub-ambient, and elevated temperatures. In 2-propanol, conversion of Form I to Form II appears to be solubility driven at ambient and sub-ambient temperatures, with little apparent change observed in the ratio of Forms I and II by XRPD analysis over 3 days. Extending the interconversion period to 8 days at room temperature left only a trace of Form I remaining. In 2-propanol, at elevated temperature, only Form II is obtained. Experiments based on 2-butanone did not have the apparent solubility limitation and gave Form II as the only observed form at sub-ambient, ambient and elevated temperatures. Based on these experiments and the DSC results, but without being bound by theory, it appears that Form II may be more stable than Form I throughout the temperature range. In addition, but without being bound by theory, the DSC results suggest that Form I and II are monotropically related.

As shown below in the Examples in Table C-1, Form I exhibited greater aqueous solubility than Form II over a pH range from 9.2 to 1.2.

When the forms of CEM-101 are dosed in a vehicle in which the compound is well solubilized, there is no observed difference in measured pharmacokinetic parameters, including Cmax, Tmax, and AUC, among Form I and Form II. When the forms of CEM-101 are dosed in a vehicle in which the compound is present as a solid, there is no statistical difference in measured pharmacokinetic parameters, including Cmax, Tmax, and AUC, among Form I and Form II.

In another embodiment, crystalline forms of CEM-101, and mixtures thereof, are described herein that show improved solubility compared to amorphous forms of CEM-101

EXAMPLES

X-Ray Powder Diffraction (XRPD) Peak Positions

XRPD patterns were collected using an Inel XRG-3000 diffractometer equipped with a curved position sensitive detector with a 2θ range of 120°. An incident beam of Cu Kα radiation (40 kV, 30 mA) was used to collect data in real time at a resolution of 0.03 °2θ. Prior to the analysis, a silicon standard (NIST SRM 640c) was analyzed to verify the Si 111 peak position. Samples were prepared for analysis by packing them into thin-walled glass capillaries. Each capillary was mounted onto a goniometer head and rotated during data acquisition. The monochromator slit was set at 5 mm by 160 μm.

Alternatively, XRPD patterns were collected using a PANalytical X'Pert Pro diffractometer. An incident beam of Cu Kα radiation was produced using an Optix long, fine-focus source. An elliptically graded multilayer mirror was used to focus the Cu Kα X-rays of the source through the specimen and onto the detector. Data were collected and analyzed using X'Pert Pro Data Collector software (v. 2.2b). Prior to the analysis, a silicon specimen (NIST SRM 640c) was analyzed to verify the Si 111 peak position. The specimen was sandwiched between 3 μm thick films, analyzed in transmission geometry, and rotated to optimize orientation statistics. A beam-stop and a helium atmosphere were used to minimize the background generated by air scattering. Soller slits were used for the incident and diffracted beams to minimize axial divergence. Diffraction patterns were collected using a scanning position-sensitive detector (X'Celerator) located 240 mm from the specimen.

The data presented herein contain X-ray diffraction patterns and tables with peak lists. It is to be understood that the range of data collected may be instrument dependent. Under typical circumstances, peaks within the range of up to about 30 °2θ are selected. Although peaks may be labeled on diffraction patterns and listed in tables, it is to be understood that different rounding algorithms may be used to round each peak to the nearest 0.1 or 0.01 °2θ, depending upon the instrument used to collect the data and/or the inherent peak resolution. Should there be a difference, the peak positions listed in the tables should be used. The location of the peaks along the x-axis (°2θ) in both the figures and the tables may be automatically determined using appropriate software, which is typically resident on the instrument used and rounded to one or two significant figures after the decimal point based upon the above criteria. Peak position variabilities are given herein to within ±0.1 °2θ based upon recommendations outlined in the USP discussion of variability in x-ray powder diffraction (United States Pharmacopeia, USP 32, NF 27, Vol. 1, pg. 392, 2009). The accuracy and precision associated with any particular measurement reported herein has not been determined. Measurements on independently prepared samples on different instruments may lead to variability which is greater than ±0.1 °2θ. For d-space listings, the wavelength used to calculate d-spacings was 1.541874 Å, a weighted average of the Cu-K$_{α1}$ and Cu-K$_{α2}$ wavelengths (*Phys. Rev.* A56(6) 4554-4568 (1997)). Variability associated with d-spacing estimates was calculated from the USP recommendation, at each d-spacing, and provided in the respective data tables.

When multiple diffraction patterns are available, then assessments of particle statistics (PS) and/or preferred orientation (PO) are possible. Reproducibility among XRPD patterns from multiple samples analyzed on a single diffractometer indicates that the particle statistics are adequate. Consistency of relative intensity among XRPD patterns from multiple diffractometers indicates good orientation statistics. Alternatively, the observed XRPD pattern may be compared with a calculated XRPD pattern based upon a single crystal structure, if available. Two-dimensional scattering patterns using area detectors can also be used to evaluate PS/PO. If the effects of both PS and PO are determined to be negligible, then the XRPD pattern is representative of the powder average intensity for the sample and prominent peaks may be identified as "Representative Peaks". In general, it is appreciated that the more data collected to determine Representative Peaks, the more statistically significant is the classification of those peaks.

CEM-101 Form I.

One PANalytical pattern and one Inel pattern were analyzed for this material, and therefore at least partially optimized orientation and particle statistic effects could be assessed through comparison with multiple patterns. The peak positions and intensities are consistent between patterns, indicating adequate particle and orientation statistics. Observed Peaks are shown in FIG. 1 and Table 1, and Representative Peaks are listed in Table 2.

TABLE 1

Observed peaks for CEM-101 Form I.

| °2θ | d-space (Å) | Intensity (%) |
|---|---|---|
| 6.19 ± 0.10 | 14.268 ± 0.234 | 13 |
| 8.47 ± 0.10 | 10.443 ± 0.125 | 30 |
| 8.80 ± 0.10 | 10.047 ± 0.115 | 68 |
| 9.34 ± 0.10 | 9.473 ± 0.102 | 10 |
| 10.52 ± 0.10 | 8.407 ± 0.080 | 100 |
| 10.97 ± 0.10 | 8.062 ± 0.074 | 46 |
| 12.04 ± 0.10 | 7.349 ± 0.061 | 25 |
| 12.41 ± 0.10 | 7.132 ± 0.058 | 43 |
| 13.20 ± 0.10 | 6.709 ± 0.051 | 88 |
| 13.68 ± 0.10 | 6.472 ± 0.047 | 41 |
| 14.52 ± 0.10 | 6.102 ± 0.042 | 22 |
| 14.85 ± 0.10 | 5.965 ± 0.040 | 22 |
| 17.02 ± 0.10 | 5.209 ± 0.031 | 45 |
| 18.03 ± 0.10 | 4.921 ± 0.027 | 46 |
| 18.61 ± 0.10 | 4.768 ± 0.026 | 71 |
| 19.48 ± 0.10 | 4.557 ± 0.023 | 48 |
| 19.73 ± 0.10 | 4.500 ± 0.023 | 56 |
| 20.68 ± 0.10 | 4.294 ± 0.021 | 38 |
| 21.17 ± 0.10 | 4.197 ± 0.020 | 39 |
| 21.89 ± 0.10 | 4.061 ± 0.018 | 53 |
| 23.41 ± 0.10 | 3.801 ± 0.016 | 25 |
| 24.44 ± 0.10 | 3.642 ± 0.015 | 11 |
| 24.91 ± 0.10 | 3.574 ± 0.014 | 37 |
| 25.61 ± 0.10 | 3.478 ± 0.013 | 18 |
| 26.35 ± 0.10 | 3.383 ± 0.013 | 11 |
| 26.80 ± 0.10 | 3.327 ± 0.012 | 24 |
| 29.04 ± 0.10 | 3.075 ± 0.010 | 18 |
| 29.96 ± 0.10 | 2.983 ± 0.010 | 10 |

TABLE 2

Representative peaks for CEM-101 Form I.

| °2θ | d-space (Å) | Intensity (%) |
|---|---|---|
| 8.80 ± 0.10 | 10.047 ± 0.115 | 68 |
| 10.52 ± 0.10 | 8.407 ± 0.080 | 100 |
| 13.20 ± 0.10 | 6.709 ± 0.051 | 88 |
| 18.61 ± 0.10 | 4.768 ± 0.026 | 71 |

CEM-101 Form II.

One Inel pattern was analyzed for this material, and preferred orientation and particle statistic effects could be assessed through comparison with the simulated pattern from single crystal data (not shown). The peak positions and intensities are consistent between patterns, indicating adequate particle and orientation statistics. Observed peaks are shown in FIG. 2 and Table 3, and representative peaks are listed in Table 4.

TABLE 3

Observed peaks for CEM-101 Form II.

| °2θ | d-space (Å) | Intensity (%) |
|---|---|---|
| 5.60 ± 0.10 | 15.772 ± 0.286 | 53 |
| 7.85 ± 0.10 | 11.260 ± 0.145 | 54 |
| 9.30 ± 0.10 | 9.505 ± 0.103 | 69 |
| 9.82 ± 0.10 | 9.004 ± 0.092 | 36 |
| 10.65 ± 0.10 | 8.304 ± 0.078 | 36 |
| 11.24 ± 0.10 | 7.871 ± 0.070 | 45 |
| 11.66 ± 0.10 | 7.592 ± 0.065 | 75 |
| 11.97 ± 0.10 | 7.395 ± 0.062 | 38 |
| 12.87 ± 0.10 | 6.880 ± 0.054 | 100 |
| 13.28 ± 0.10 | 6.666 ± 0.050 | 33 |

TABLE 3-continued

Observed peaks for CEM-101 Form II.

| °2θ | d-space (Å) | Intensity (%) |
|---|---|---|
| 13.77 ± 0.10 | 6.432 ± 0.047 | 32 |
| 14.15 ± 0.10 | 6.260 ± 0.044 | 36 |
| 14.63 ± 0.10 | 6.054 ± 0.041 | 35 |
| 15.12 ± 0.10 | 5.861 ± 0.039 | 48 |
| 16.71 ± 0.10 | 5.306 ± 0.032 | 78 |
| 17.23 ± 0.10 | 5.147 ± 0.030 | 33 |
| 17.50 ± 0.10 | 5.067 ± 0.029 | 36 |
| 18.37 ± 0.10 | 4.830 ± 0.026 | 38 |
| 18.58 ± 0.10 | 4.776 ± 0.026 | 43 |
| 18.78 ± 0.10 | 4.724 ± 0.025 | 40 |
| 19.34 ± 0.10 | 4.590 ± 0.024 | 37 |
| 19.68 ± 0.10 | 4.510 ± 0.023 | 46 |
| 20.62 ± 0.10 | 4.308 ± 0.021 | 38 |
| 20.97 ± 0.10 | 4.237 ± 0.020 | 43 |
| 21.17 ± 0.10 | 4.196 ± 0.020 | 47 |
| 21.38 ± 0.10 | 4.156 ± 0.019 | 35 |
| 21.83 ± 0.10 | 4.071 ± 0.019 | 34 |
| 22.11 ± 0.10 | 4.021 ± 0.018 | 34 |
| 22.59 ± 0.10 | 3.936 ± 0.017 | 27 |
| 23.32 ± 0.10 | 3.815 ± 0.016 | 32 |
| 23.49 ± 0.10 | 3.787 ± 0.016 | 32 |
| 24.15 ± 0.10 | 3.685 ± 0.015 | 28 |
| 24.43 ± 0.10 | 3.644 ± 0.015 | 32 |
| 24.77 ± 0.10 | 3.594 ± 0.014 | 30 |
| 25.61 ± 0.10 | 3.479 ± 0.013 | 30 |
| 25.78 ± 0.10 | 3.456 ± 0.013 | 29 |
| 26.23 ± 0.10 | 3.398 ± 0.013 | 27 |
| 26.58 ± 0.10 | 3.354 ± 0.012 | 25 |
| 27.23 ± 0.10 | 3.275 ± 0.012 | 26 |
| 27.55 ± 0.10 | 3.238 ± 0.012 | 26 |
| 27.86 ± 0.10 | 3.203 ± 0.011 | 31 |
| 28.52 ± 0.10 | 3.130 ± 0.011 | 24 |
| 29.49 ± 0.10 | 3.029 ± 0.010 | 26 |

TABLE 4

Representative peaks for CEM-101 Form II.

| °2θ | d-space (Å) | Intensity (%) |
|---|---|---|
| 5.60 ± 0.10 | 15.772 ± 0.286 | 53 |
| 7.85 ± 0.10 | 11.260 ± 0.145 | 54 |
| 9.30 ± 0.10 | 9.505 ± 0.103 | 69 |
| 11.66 ± 0.10 | 7.592 ± 0.065 | 75 |
| 12.87 ± 0.10 | 6.880 ± 0.054 | 100 |
| 16.71 ± 0.10 | 5.306 ± 0.032 | 78 |

Recrystallization Studies

Recrystallization conditions that yield Form I and Form II, as well as conditions which afford amorphous material or mixtures of Form I and Form II, as well as the outputs (recoveries) from the conditions are shown in the following Table A. Recrystallization Studies. The polymorph form was determined by analysis of the X-ray powder diffraction pattern for each isolated product. In the table, "T" represents the ratio of solvent to the mass of solid in mL/mg (or L/g); DCM means dichloromethane; DMF means dimethylformamide; and IPE means isopropylether.

TABLE A

Recrystallization Study Results

| Experiment | CEM-101 Input | Solvent | | Procedure | CEM-101 Output | Polymorph Form |
|---|---|---|---|---|---|---|
| 1 | 5 g | Acetone (5T) | Water (10T) | Dissolved solid in acetone and added water dropwise at 30° C. | 4.5 g | Form II |
| 2 | 5 g | DCM (5T) | | Dissolved in DCM and freeze dried | 4.4 g | Amorphous |
| 3 | 5 g | Acetone (5T) | Water (50T) | Dissolved solid in acetone and added to water dropwise at 30° C. | 4.4 g | Form I + Form II |
| 4 | 2 g | DMF(2T) | Water (50T) | Dissolved solid in DMF and added to water dropwise at 28° C. | 1.8 g | Form I |
| 5 | 3 g | Methanol (18T) | Water (18T) | Dissolved solid in methanol and added water dropwise at 28° C. | 2.5 g | Form II |
| 6 | 3 g | Ethanol (10T) | Water (10T) | Dissolved solid in ethanol and added water dropwise at 28° C. | 2.2 g | Form II |
| 7 | 3 g | Methanol (18T) | | Dissolved in methanol and freeze dried | 2.7 g | Form II + Form I |
| 8 | 3 g | DCM (3T) | Cyclohexane (20T) | Dissolved solid in DCM and added to cyclohexane in one portion at 28° C. | 2.3 g | Form II |
| 9 | 3 g | Ethanol (10T) | IPE (33T) | Dissolved solid in ethanol and added to IPE in one portion at 28° C. | 1.2 g | Form II |
| 10 | 2 g | Acetonitrile (4T) | | Dissolved solid in acetonitrile and cooled to 30° C. | 0.6 g | Form I + Form II |
| 11 | 2 g | 1,4-Dioxane (5T) | Water (5T) | Dissolved solid in 1,4-Dioxane at 70° C. and added water at 0° C. to 5° C. | 2.1 | Form II |
| 12 | 2 g | Acetonitrile (4T) | Water (4T) | Dissolved solid in acetonitrile at 80° C. and added water at 55° C. | 1.6 g | Form II |

TABLE A-continued

Recrystallization Study Results

| Experiment | CEM-101 Input | Solvent | | Procedure | CEM-101 Output | Polymorph Form |
|---|---|---|---|---|---|---|
| 13 | 1 g | Acetonitrile (4T) | | Dissolved solid in acetonitrile at 80° C. and seeded with 10 mg of Form I | 0.5 g | Form II + Form I |
| 14 | 1 g | Acetonitrile (4T) | | Dissolved solid in acetonitrile at 80° C. and seeded with 100 mg of Form I | 0.4 g | Form II |
| 15 | 12 g | DCM (3T) | | Dissolved in DCM and freeze dried | 9.3 g | Amorphous |
| 16 | 1 g | Ethanol (15T) | Water (5T) | Dissolved solid (Form I) in ethanol (15 mL) in 65° C., reduced volume to 5 mL and added water (5 mL) dropwise at 28° C. | 0.8 g | Form II |
| 17 | 2 g | DMF(2T) | Water (50T) | Dissolved solid (Form II) in DMF (4 mL) and added to water (100 mL) dropwise at 28° C. | 1.9 g | Form I + Form II |
| 18 | 5 g | Acetone (7T) | Water (50T) | Dissolved solid (Form II) in acetone (35 mL) in 65° C., reduced volume to 20 mL and added to water (100 mL) dropwise at 28° C. The wet solid was suspended in water and stirred under heating at 65° C., cooled and filtered. | 4.9 g | Form I |
| 19 | 2 g | Water | | Dissolved solid (Form II) in water (100 mL) and stirred under heating at 60° C., cooled and filtered. | 1.8 g | Form II |
| 20 | 5 g | Ethanol (15T) | Water (5T) | Dissolved solid (Form II) in ethanol (75 mL) at 65° C., reduced volume to 35 mL and added water dropwise at 60° C. Ethanol was removed by distillation after formation of the solid, stirring under heating, cooled and filtered. | 4.8 g | Unknown |
| 21 | 5 g | Acetone (6T) | Water (60T) | Dissolved solid (Form I + II) in acetone (30 mL) at 65° C., filtered, reduced volume to 20 mL and added to water (300 mL) dropwise at 27° C., stirred and filtered. | 4.5 g | Form I |
| 22 | 5 g | Acetone (8T) | Water (60T) | Dissolved solid (Form I + II) in acetone (40 mL) at 65° C., filtered, reduced volume to 30 mL and added to water (450 mL) dropwise at 27° C., stirred and filtered. | 4.5 g | Form I |
| 23 | 2 g | Ethanol (15T) | Water (60T) | Dissolved solid (Form I + II) in ethanol (30 mL) at 65° C., filtered, reduced volume to 16 mL and added to water (120 mL) dropwise at 27° C., stirred and filtered. | 1.7 g | Form I |
| 24 | 5 g | Acetone (6T) | Water (60T) | Dissolved solid (Form I + II) in acetone (30 mL) at 65° C., filtered, reduced volume to 20 mL and water (300 mL) was added dropwise at 27° C., stirred and filtered. | 4.4 g | Form II |
| 25 | 5 g | Acetone (7T) | Water (50T) | Dissolved solid (Form I + II) in acetone (35 mL) at 65° C., filtered, reduced volume to 25 mL and added to water (250 mL) | 4.5 g | Form I + little of Form II |

TABLE A-continued

Recrystallization Study Results

| Experiment | CEM-101 Input | Solvent | Procedure | | CEM-101 Output | Polymorph Form |
|---|---|---|---|---|---|---|
| 26 | 5 g | Ethanol (15T) | Water (50T) | dropwise at 27° C., stirred and filtered. Dissolved solid (Form I + II) in ethanol (75 mL) at 65° C., filtered, reduced volume to 40 mL and added to water (250 mL) dropwise at 27° C., stirred and filtered. | 4.4 g | Form I |

Hot Stage Microscopy and DSC

Form I of CEM-101 exhibits a melt onset at about 180° C. and final melt at about 200° C. by hot stage microscopy and exhibits endothermic events at 170 and 197-198° C. by differential scanning calorimetry (DSC). Form II of CEM-101 exhibits a melt onset at about 215° C. by hot stage microscopy and a DSC peak at about 225° C., as a single endothermic event. Mixtures of varying amounts of Form I and Form II have exhibited endothermic events at 194-199 and at 219-225° C. by DSC, depending upon the ratio of the forms. It is to be understood that hot stage microscopy and/or DSC may be used to determine the presence or absence of certain forms in the compounds and compositions described herein.

Interconversion Studies.

Interconversion studies by slurrying of Form I and Form II are shown in the following Table B in which the starting solid was a mixture of Form I and Form II; IPA is isopropyl alcohol (isopropanol) and MEK is methyl ethyl ketone (2-butanone).

TABLE B

Interconversion Slurries for CEM-101 Form A and B Solids

| Solvent | Conditions[a] | XRPD Result[b] |
|---|---|---|
| IPA | 60° C. 3 days | Form II |
|  | RT 3 days | Form I + II |
|  | RT 5 days[c] (8 days total) | Form II + trace Form I |
|  | 2-8° C. 3 days | Form I + II |
|  | 2-8° C. 5 days[d] (8 days total) | Form I + II |
| MEK | 60° C. 3 days | IS[b] |
|  | 60° C. 3 days[c] (6 days total) | Form II |
|  | RT 3 days | Form II |
|  | 2-8° C. 3 days | Form II |

[a]Reported times and temperatures are approximate. RT = ambient temperature.
[b]XRPD = X-ray powder diffraction, IS = insufficient solids for analysis.
[c]Continuation of previous slurry with additional solids.
[d]Continuation of previous slurry.

Aqueous Solubility.

Using a linear calibration curve obtained by plotting the concentration of CEM-101 vs. LC/MS-MS peak areas, the aqueous solubility of forms of CEM-101 are obtained as follows: Test compounds (dry powder) are added to 0.9% saline (initial pH 6.03) until precipitation, and the mixture is incubated for 6 h with shaking. After the incubation period, the samples are centrifuged twice and solubility is estimated using the linearity standard curve for the compound: Form I showed a solubility of 1411 µg/mL.

Using a linear calibration curve obtained by plotting the concentration of CEM-101 vs. LC/MS-MS peak areas, the aqueous solubility of forms of CEM-101 was obtained as follows: Test compounds (dry powder) were added to water with the indicated pH until precipitation, and the mixture was incubated for 6 h with shaking. After the incubation period, the samples were centrifuged twice and solubility was estimated using the linearity standard curve for the compound: Media: Water at pH: pH 9.2, 7.4, 4 and 1.2 (adjusted using 0.1N NaOH and 0.1 N HCl); Incubation: 6 h at 26° C. with shaking; Test concentrations: Dry powder added till saturation; Detection: LC/MS-MS. The results are shown in Table C-1.

TABLE C-1

Aqueous Solubility Study

| pH | Form II (µg/mL) | Form I (µg/mL) |
|---|---|---|
| 9.2 | 331 | 1751 |
| 7.4 | 305 | 2224 |
| 4 | 361 | 4656 |
| 1.2 | 3638 | 4808 |

Intrinsic Dissolution Comparison.

Mean intrinsic dissolution rates for exemplary batches of the two forms are shown in Table C-2 for 3 batches of Form I (SD and % CV for one batch shown) and for Form II.

TABLE C-2

Mean Intrinsic Dissolution Studies.

Mean intrinsic dissolution rate (mg/min/cm$^2$)

| | Form I | | | | | Form II | |
|---|---|---|---|---|---|---|---|
| Dissolution Medium | Batch A | Batch B | Batch C | SD* | % CV* | SD | % CV |
| 0.1N Hydrochloric Acid | 9.4 | 10.6 | 7.9 | 35.8 | 9.8 | 8.8 | 38.0 | 9.4 |
| Acetate buffer, pH 4.5 | 2.1 | 2.8 | 2.7 | 6.43 | 5.2 | 2.7 | 6.4 | 10.3 |

TABLE C-2-continued

Mean Intrinsic Dissolution Studies.

Mean intrinsic dissolution rate (mg/min/cm$^2$)

| Dissolution Medium | Form I Batch A | Form I Batch B | Form I Batch C | SD* | % CV* | Form II | SD | % CV |
|---|---|---|---|---|---|---|---|---|
| Phosphate buffer, pH 6.8 | 0.004 | 0.03 | 0.02 | 0.53 | 53.0 | 0.01 | 0.5 | 51.1 |
| Phosphate buffer, pH 7.6 | 0.02 | 0.001 | ND | NA | NA | ND | NA | NA |
| Water | 2.0 | 0.7 | 1.6 | 4.91 | 9.6 | ND | NA | NA |

*SD and CV % for Batch C only. ND, not determined. NA, not applicable.

Pharmacokinetic Evaluation of CEM-101 in Balb/c Mice.

The pharmacokinetics of lots of CEM-101 characterized as Form I and Form II were evaluated in Balb/c mice receiving a singe dose of 20 or 100 mg/kg body weight (b.w.) via oral gavage. The doses were prepared as 2.0 mg/mL or 10.0 mg/mL in a vehicle of 0.5% (w/v) carboxymethyl cellulose in water and a dose volume of 10 mL/kg b.w. Blood samples were collected at various time points during the next 6 h post dose. The results are shown as follows:

Table D: Plasma Concentrations of CEM-101 in μg/mL Vs. Time in Female Balb/c Mouse at 20 Mg/Kg b.w.

TABLE D

CEM-101 Form I and Form II Polymorphs
Oral pharmacokinetics studies in female Balb/c mouse (20 mg/kg b.w.)
Plasma concentrations (μg/mL); Female Balb/c mouse (20 mg/kg b.w.)

| Time (h) | CEM-101 Form II Mean Stdv | CEM-101 Form I Mean Stdv |
|---|---|---|
| 0.00 | 0.0 ± 0.0 | 0.0 ± 0.0 |
| 0.25 | 6.2 ± 1.6 | 8.2 ± 2.4 |
| 0.50 | 8.8 ± 0.8 | 13.6 ± 2.0 |
| 1.00 | 7.3 ± 0.9 | 12.0 ± 1.7 |
| 2.00 | 6.1 ± 1.0 | 11.3 ± 1.4 |
| 4.00 | 5.5 ± 1.7 | 7.7 ± 0.7 |
| 6.00 | 1.3 ± 0.5 | 4.2 ± 0.4 |

Table E: Plasma Concentrations of CEM-101 in μg/mL Vs. Time in Male Balb/c Mouse at 20 Mg/Kg b.w.

TABLE E

CEM-101 Form I and Form II Polymorphs
Oral pharmacokinetics studies in male Balb/c mouse (20 mg/kg b.w.)
Plasma concentrations (μg/mL); Male Balb/c mouse (20 mg/kg b.w.)

| Time (h) | CEM-101 Form II Mean Stdv | CEM-101 Form I Mean Stdv |
|---|---|---|
| 0.00 | 0.0 ± 0.0 | 0.0 ± 0.0 |
| 0.25 | 4.1 ± 0.8 | 5.3 ± 1.8 |
| 0.50 | 6.7 ± 0.6 | 7.7 ± 1.6 |
| 1.00 | 5.9 ± 0.8 | 9.5 ± 0.9 |
| 2.00 | 5.6 ± 0.4 | 6.4 ± 0.8 |
| 4.00 | 4.9 ± 1.1 | 5.9 ± 0.6 |
| 6.00 | 2.9 ± 0.6 | 2.6 ± 0.8 |

Table F: Plasma Concentrations of CEM-101 in μg/mL Vs. Time in Female Balb/c Mouse at 100 Mg/Kg b.w.

TABLE F

CEM-101 Form I and Form II Polymorphs
Oral pharmacokinetics studies in female Balb/c mouse (100 mg/kg b.w.)
Plasma concentrations (μg/mL); Female Balb/c mouse (100 mg/kg b.w.)

| Time (h) | CEM-101 Form II Mean Stdv | CEM-101 Form I Mean Stdv |
|---|---|---|
| 0.00 | 0.0 ± 0.0 | 0.0 ± 0.0 |
| 0.25 | 7.3 ± 0.9 | 11.9 ± 1.7 |
| 0.50 | 10.5 ± 1.4 | 11.6 ± 1.6 |
| 1.00 | 9.6 ± 2.2 | 14.7 ± 2.3 |
| 2.00 | 9.5 ± 2.2 | 14.1 ± 2.9 |
| 4.00 | 10.2 ± 1.0 | 16.0 ± 2.3 |
| 6.00 | 7.8 ± 1.1 | 19.5 ± 2.3 |

Table G: Plasma Concentrations of CEM-101 in μg/mL Vs. Time in Male Balb/c Mouse at 100 Mg/Kg b.w.

TABLE G

CEM-101 Form I and Form II Polymorphs
Oral pharmacokinetics studies in female Balb/c mouse (100 mg/kg b.w.)
Plasma concentrations (μg/mL); Male Balb/c mouse (100 mg/kg b.w.)

| Time (h) | CEM-101 Form II Mean Stdv | CEM-101 Form I Mean Stdv |
|---|---|---|
| 0.00 | 0.0 ± 0.0 | 0.0 ± 0.0 |
| 0.25 | 6.8 ± 0.7 | 11.3 ± 2.5 |
| 0.50 | 6.9 ± 1.1 | 10.7 ± 3.0 |
| 1.00 | 8.7 ± 2.7 | 13.1 ± 3.2 |
| 2.00 | 9.3 ± 1.2 | 13.4 ± 3.1 |
| 4.00 | 10.6 ± 1.4 | 17.4 ± 2.9 |
| 6.00 | 7.2 ± 0.8 | 12.0 ± 2.0 |

Table H: Mean Plasma PK Parameters at 20 Mg/Kg.

TABLE H

CEM-101 Form I and Form II Polymorphs
Oral pharmacokinetics studies in Balb/c mouse
Mean Plasma PK Parameters

| Parameters | Male - 20 mg/kg CEM-101 Form II | Male - 20 mg/kg CEM-101 Form I | Female - 20 mg/kg CEM-101 Form II | Female - 20 mg/kg CEM-101 Form I |
|---|---|---|---|---|
| Route of administration | Oral | Oral | Oral | Oral |
| Dose (mg/kg) | 20 | 20 | 20 | 20 |
| Cmax (μg/mL) | 6.73 | 9.5 | 8.8 | 13.6 |
| Tmax (h) | 0.5 | 1 | 0.5 | 0.5 |
| AUClast (h * μg/mL) (0 to 6 h) | 29 | 35 | 31.6 | 53 |
| AUCinf (h * μg/mL) | 49 | 46 | 36 | 70 |
| AUCextrap (%) | 42 | 24 | 12 | 24 |

Table I: Mean Plasma PK Parameters at 100 Mg/Kg.

TABLE I

CEM-101 Form I and Form II Polymorphs
Oral pharmacokinetics studies in Balb/c mouse
Mean Plasma PK Parameters

| | Male - 100 mg/kg | | Female - 100 mg/kg | |
|---|---|---|---|---|
| Parameters | CEM-101 Form II | CEM-101 Form I | CEM-101 Form II | CEM-101 Form I |
| Route of administration | Oral | Oral | Oral | Oral |
| Dose (mg/kg) | 100 | 100 | 100 | 100 |
| Cmax (μg/mL) | 10.6 | 17.4 | 10.5 | 19.5 |
| Tmax (h) | 4 | 4 | 4 | 6 |
| AUClast (h * μg/mL) (0 to 6 h) | 66 | 83.5 | 55 | 91 |
| AUCinf (h * μg/mL) | 99 | NC | NC | NC |
| AUCextrap (%) | 33 | NC | NC | NC |

Pharmacokinetic (PK) Comparison.

Results of a further oral pharmacokinetic study of Form I and Form II in groups of 5 female Balb/c mice receiving a singe dose at 5, 10 and 20 mg/kg is are shown in Table J.

TABLE J

Mean Plasma PK Parameters

| | | Dosing | | | | | | | | | | | |
|---|---|---|---|---|---|---|---|---|---|---|---|---|---|
| | | 5 mg/kg | | | | 10 mg/kg | | | | 20 mg/kg | | | |
| Form | c | t½ | Tmax | Cmax | AUC 0-24 | t½ | Tmax | Cmax | AUC 0-24 | t½ | Tmax | Cmax | AUC 0-24 |
| I | N | 1 | 5 | 5 | 5 | 4 | 5 | 5 | 5 | 4 | 5 | 5 | 5 |
| | Mean | 1.32 | 0.600 | 1.43 | 3.30 | 3.60 | 2.40 | 4.68 | 17.7 | 2.10 | 1.60 | 6.64 | 26.2 |
| | SD | NC | 0.224 | 0.249 | 0.551 | 1.65 | 0.894 | 1.31 | 3.25 | 0.509 | 0.548 | 1.84 | 4.84 |
| | Min | 1.32 | 0.500 | 1.02 | 2.78 | 2.44 | 2.00 | 3.21 | 14.4 | 1.73 | 1.00 | 4.66 | 19.5 |
| | Median | 1.32 | 0.500 | 1.54 | 3.16 | 2.95 | 2.00 | 4.09 | 17.2 | 1.91 | 2.00 | 5.91 | 26.7 |
| | Max | 1.32 | 1.00 | 1.65 | 4.24 | 6.05 | 4.00 | 6.11 | 21.1 | 2.85 | 2.00 | 9.34 | 33.0 |
| | CV % | NC | 37.3 | 17.4 | 16.7 | 46.0 | 37.3 | 27.9 | 18.3 | 24.2 | 34.2 | 27.7 | 18.5 |
| II | N | 5 | 5 | 5 | 5 | 3 | 5 | 5 | 5 | 2 | 5 | 5 | 5 |
| | Mean | 1.17 | 1.20 | 1.85 | 4.69 | 1.42 | 1.25 | 2.63 | 7.58 | 2.46 | 1.10 | 5.36 | 20.1 |
| | SD | 0.297 | 0.447 | 0.249 | 0.819 | 0.263 | 0.750 | 1.22 | 2.27 | 0.0517 | 0.548 | 0.837 | 3.33 |
| | Min | 0.935 | 1.00 | 1.55 | 4.21 | 1.12 | 0.250 | 1.50 | 4.62 | 2.43 | 0.500 | 3.88 | 16.3 |
| | Median | 1.12 | 1.00 | 1.80 | 4.31 | 1.53 | 1.00 | 2.42 | 7.59 | 2.46 | 1.00 | 5.66 | 21.7 |
| | Max | 1.67 | 2.00 | 2.12 | 6.14 | 1.61 | 2.00 | 4.69 | 10.0 | 2.50 | 2.00 | 5.96 | 23.4 |
| | CV % | 25.3 | 37.3 | 13.5 | 17.5 | 18.5 | 60.0 | 46.3 | 30.0 | 2.10 | 49.8 | 15.6 | 16.6 |

Examples of Pharmaceutical Compositions Using CEM-101 Form I

The following formulation is used to provide Size 0 hard gelatin capsules containing 200 mg of CEM-101 per capsule.

| Material | % w/w | Qty/Cap (mg) |
|---|---|---|
| CEM-101 | 61.54 | 200.00 |
| Avicel PH101 | 30.96 | 100.63 |
| Plasdone K29/32 | 2.00 | 6.50 |
| Ac-Di-Sol | 4.00 | 13.00 |
| Sodium Lauryl Sulfate, NF | 1.00 | 3.25 |
| Magnesium Stearate, NF (Vegetable Grade) | 0.50 | 1.63 |
| Purified Water,* USP | 64.3 | — |
| Total | 100.00 | 325.00 |

*Estimated amount of purified water. Removed during processing; not in final formula.

The following formulation is used to provide tablets containing 200 mg per tablet, containing 54% drug load and a target weight of 370 mg/tablet. The drug product is manufactured by wet granulation and the tablets are compressed at 6 kp.

| Material | % w/w | Qty/Tablet (mg) |
|---|---|---|
| CEM-101* (Intra-granular) | 54.04 | 200.00 |
| Avicel PH101 (Intra-granular) | 18.00 | 66.60 |
| Sodium Lauryl Sulfate (Intra-granular) | 1.00 | 3.70 |
| Plasdone K29/32 (Intra-solution) | 3.00 | 11.10 |
| Pearlitol 200SD (Extra-granular) | 17.95 | 66.40 |
| Ac-Di-Sol (Extra-granular) | 5.00 | 18.50 |
| Cab-O-Sil (Extra-granular) | 0.50 | 1.85 |
| Magnesium Stearate (Vegetable Grade) (Extra-granular) | 0.50 | 1.85 |
| Purified Water** | | |
| Total: | 100.00 | 370.00 |

*Adjusted for potency
**Removed during processing, not in final formulation.

Example

The stability of Form I and Form II of CEM-101 was evaluated under various conditions, as shown in the following Tables. In each case, there was no observed change in color of the test material during the entire study. In each case, the test material was first placed in Primary Packaging Material (LLDPE bag within a HMHDPE/LDPE/LDPE blend bag, and then heat sealed). The Primary Packaging Material was placed in Secondary Packaging Material (HDPE drum). All other impurities were less than 1% at each time point.

|  | Initial | 3 Month | 6 Month | 9 Month | 12 Month |
|---|---|---|---|---|---|
| Form II, 2-8° C. | | | | | |
| Water | 1.01% | 1.24% | 1.39% | 1.38% | 1.37% |
| Chromatographic Purity | 97.0 | 96.0 | 96.8 | 96.4 | 96.8 |
| 3-Ethynylaniline | Not Detected | Not Detected | Not Detected | 0.01% | 0.12% |
| Assay (on hydrous basis) | 93.9 | 93.4 | 93.6 | 93.3 | 93.0 |
| Form II, 25° C./60% RH | | | | | |
| Water | 1.01% | 1.16% | 1.42% | 1.45% | 1.48% |
| Chromatographic Purity | 97.0% | 96.0% | 96.7% | 96.2% | 96.1% |
| 3-Ethynylaniline | Not Detected | Not Detected | Not Detected | 0.04% | 0.11% |
| Assay (on hydrous basis) | 93.9% | 93.6% | 93.7% | 93.2% | 93.0% |
| Form II, 40° C./75% RH | | | | | |
| Water | 1.01% | 1.24% | 1.62% | 1.51% | 1.56% |
| Chromatographic Purity | 97.0% | 95.9% | 96.5% | 96.2% | 97.1% |
| 3-Ethynylaniline | Not Detected | Not Detected | Not Detected | 0.02% | 0.05% |
| Assay (on hydrous basis) | 93.9% | 93.0% | 93.1% | 92.5% | 92.3% |

|  | Initial | 3 Month | 6 Month | 12 Month |
|---|---|---|---|---|
| Form I (Lot 3), 2-8° C. | | | | |
| Water | 1.11% | 1.63% | 1.61% | 1.69% |
| Chromatographic Purity | 98.3% | 98.1% | 98.4% | 98.5% |
| 3-Ethynylaniline | 0.01% | 0.01% | Not Detected | Not Detected |
| Assay (on hydrous basis) | 99.5% | 98.9% | 98.8% | 98.7% |
| Form I (Lot 3), 25° C./60% RH | | | | |
| Water | 1.11% | 1.65% | 1.71% | 1.75% |
| Chromatographic Purity | 98.3% | 98.1% | 98.3% | 98.4% |
| 3-Ethynylaniline | 0.01% | 0.01% | Not Detected | Not Detected |
| Assay (on hydrous basis) | 99.5% | 98.7% | 98.6% | 98.5% |

|  | Initial | 3 Month | 12 Month |
|---|---|---|---|
| Form I (Lot 3), 40° C./75% RH | | | |
| Water | 1.11% | 1.68% | 1.84% |
| Chromatographic Purity | 98.3% | 98.0% | 98.3% |
| 3-Ethynylaniline | 0.01% | 0.01% | 0.01% |
| Assay (on hydrous basis) | 99.5% | 98.5% | 98.3% |

|  | Initial | 3 Month | 6 Month | 12 Month |
|---|---|---|---|---|
| Form I (Lot 4), 2-8° C. | | | | |
| Water | 0.92% | 1.56% | 1.47% | 1.51% |
| Chromatographic Purity | 98.2% | 98.1% | 98.3% | 98.4% |
| 3-Ethynylaniline | 0.01% | 0.01% | 0.01% | Not Detected |
| Assay (on hydrous basis) | 99.0% | 98.4% | 98.3% | 98.2% |
| Form I (Lot 4), 25° C./60% RH | | | | |
| Water | 0.92% | 1.59% | 1.75% | 1.78% |
| Chromatographic Purity | 98.2% | 98.1% | 98.4% | 98.4% |
| 3-Ethynylaniline | 0.01% | 0.01% | Not Detected | Not Detected |
| Assay (on hydrous basis) | 99.0% | 98.3% | 98.2% | 98.1% |

-continued

| Form I (Lot 4), 40° C./75% RH | | | |
|---|---|---|---|
| | Initial | 3 Month | 12 Month |
| Water | 0.92% | 1.65% | 1.82% |
| Chromatographic Purity | 98.2% | 98.4% | 98.3% |
| 3-Ethynylaniline | 0.01% | 0.01% | 0.01% |
| Assay (on hydrous basis) | 99.0% | 98.2% | 98.1% |

What is claimed is:

1. A process for the preparation of Form I of CEM-101, the process comprising the step of adding a solution of CEM-101 in a water miscible, polar organic solvent to water at a temperature below 50° C.

2. The process of claim 1 wherein the Form I of CEM-101 is substantially free of other physical forms.

3. The process of claim 1 further comprising one or more of the following steps:
    heating the solution of CEM-101;
    filtering the solution of CEM-101;
    reducing the volume of the solution of CEM-101 by evaporation; and
    stirring the water during addition of the solution of CEM-101.

4. The process of claim 1 wherein the solvent is acetone, methanol or ethanol, or a combination thereof.

5. The process of claim 1 wherein the solvent is acetone.

6. The process of claim 1 wherein the solution is added to water at a temperature of about 10° C. to about 30° C.

7. A process for the preparation of Form II of CEM-101, the process comprising the step of adding water to a solution of CEM-101 in a water miscible, polar organic solvent.

8. The process of claim 7 wherein the Form II of CEM-101 is substantially free of other physical forms.

9. The process of claim 7 further comprising one or more of the following steps:
    filtering the solution of CEM-101;
    reducing the volume of the solution of CEM-101 by evaporation; and
    stirring the solution of CEM-101 during addition of the water.

10. The process of claim 7 wherein the solvent is acetone, acetonitrile, 1,4-dioxane, methanol or ethanol, or a combination thereof.

11. The process of claim 7 wherein the solution of CEM-101 is above ambient temperature.

12. A process of purifying CEM-101 comprising converting one or more forms or mixtures of forms of the CEM-101 into Form I or Form II substantially free of other physical forms.

13. The process of claim 12 further comprising the step of adding a solution of the CEM-101 in a water miscible, polar organic solvent to water at a temperature below 50° C.

14. The process of claim 12 further comprising the step of adding water to a solution of the CEM-101 in a water miscible, polar organic solvent.

* * * * *